United States Patent [19]

Sawyer

[11] Patent Number: 4,883,461
[45] Date of Patent: Nov. 28, 1989

[54] SAFETY NEEDLE SHEATH IN ANTI-REFLUX CATHETER HAVING NOVEL VALVE MEANS

[75] Inventor: Philip N. Sawyer, Brooklyn, N.Y.

[73] Assignee: Interface Biomedical Laboratories Corp., Brooklyn, N.Y.

[21] Appl. No.: 269,829

[22] Filed: Nov. 10, 1988

Related U.S. Application Data

[63] Continuation-in-part of Ser. No. 50,589, May 15, 1987, Pat. No. 4,784,644.

[51] Int. Cl.⁴ ............................................. A61M 5/00
[52] U.S. Cl. ................................. 604/53; 604/169; 604/198; 604/247
[58] Field of Search ............... 604/122, 197, 198, 263, 604/164, 165, 167, 169, 53, 247

[56] References Cited

U.S. PATENT DOCUMENTS

| | | | |
|---|---|---|---|
| 220,559 | 10/1879 | Wilson | 137/843 |
| 1,696,018 | 12/1928 | Schellberg | 604/43 |
| 2,786,642 | 3/1957 | Comb | 251/50 |
| 2,988,103 | 6/1961 | Canvasser | 137/218 |
| 3,097,646 | 7/1963 | Scislowicz . | |
| 3,298,391 | 1/1967 | Savage | 137/493 |
| 3,441,245 | 4/1969 | Holland et al. | 251/5 |
| 3,469,582 | 9/1969 | Jackson | 251/5 |
| 3,543,752 | 12/1970 | Hesse | 604/123 |
| 3,672,372 | 6/1972 | Heimlich . | |
| 3,687,365 | 8/1972 | Laessig | 236/99 |
| 3,717,174 | 2/1973 | Dewall | 604/34 |
| 3,769,982 | 11/1973 | Schulte . | |
| 3,833,013 | 9/1974 | Leonard | 137/171 |
| 3,888,249 | 6/1975 | Spencer . | |
| 3,967,645 | 7/1976 | Gregory | 137/525.1 |
| 3,991,768 | 11/1976 | Portnoy | 128/350 V |
| 4,062,360 | 12/1977 | Bentley . | |
| 4,096,860 | 6/1978 | McLaughlin | 604/44 |
| 4,103,686 | 8/1978 | LeFevre . | |
| 4,103,689 | 8/1978 | Leighton . | |
| 4,108,175 | 8/1978 | Orton | 604/168 |
| 4,111,047 | 9/1978 | Bailey | 137/843 |
| 4,126,132 | 11/1978 | Portner et al. | 604/123 |
| 4,134,402 | 1/1979 | Mahurkar . | |
| 4,243,034 | 1/1981 | Brandt | 604/169 |
| 4,245,635 | 1/1981 | Kontos . | |
| 4,300,552 | 11/1981 | Cannon . | |
| 4,303,100 | 12/1981 | Kalb | 251/5 |
| 4,324,239 | 4/1982 | Gordon et al. . | |
| 4,336,800 | 6/1982 | Giovanni | 604/123 |
| 4,385,631 | 5/1983 | Uthmann | 604/284 |
| 4,468,224 | 8/1984 | Enzmann et al. | 604/247 |
| 4,496,350 | 1/1985 | Cosentino | 604/175 |
| 4,501,531 | 2/1985 | Bilstad et al. | 604/123 |
| 4,502,502 | 3/1985 | Krug | 604/247 |
| 4,515,589 | 5/1985 | Austin et al. | 604/122 |
| 4,535,773 | 8/1985 | Yoon | 604/169 |
| 4,535,818 | 8/1985 | Duncan | 137/846 |
| 4,540,027 | 9/1985 | Forberg | 137/848 |
| 4,568,333 | 2/1986 | Sawyer et al. | 604/122 |
| 4,571,241 | 2/1986 | Christopher | 604/104 |
| 4,684,364 | 8/1987 | Sawyer et al. | 604/123 |
| 4,722,725 | 2/1988 | Sawyer et al. | 604/122 |

FOREIGN PATENT DOCUMENTS

| | | | |
|---|---|---|---|
| 1052659 | 4/1979 | Canada . | |
| 2513490 | 10/1975 | Fed. Rep. of Germany | 604/5 |
| 0592193 | 7/1925 | France | 604/44 |
| 509746 | 6/1969 | U.S.S.R. | 137/843 |
| 555251 | 6/1977 | U.S.S.R. . | |
| 1510191 | 5/1978 | United Kingdom . | |

OTHER PUBLICATIONS

Jagger et al., "Rates of Needle-Stick Injury Caused by Various Devices in a University Hospital", The New England Journal of Medicine, Aug. 4, 1988, pp. 284–287.

Primary Examiner—Stephen C. Pellegrino
Attorney, Agent, or Firm—Pennie & Edmonds

[57] ABSTRACT

Methods for preventing needle-stick injuries to health-care workers during intravenous or intra-arterial procedures as well as for preventing catheter-contamination and blood clotting within the tip of the catheter. Also, novel fluid directing means and catheters which include integral fluid flow control means for use in these methods.

20 Claims, 2 Drawing Sheets

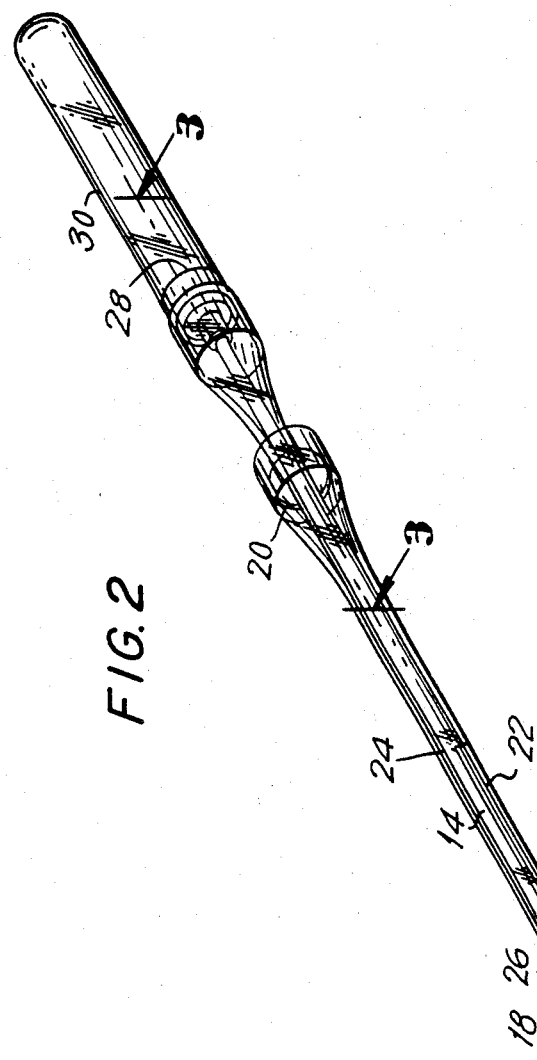
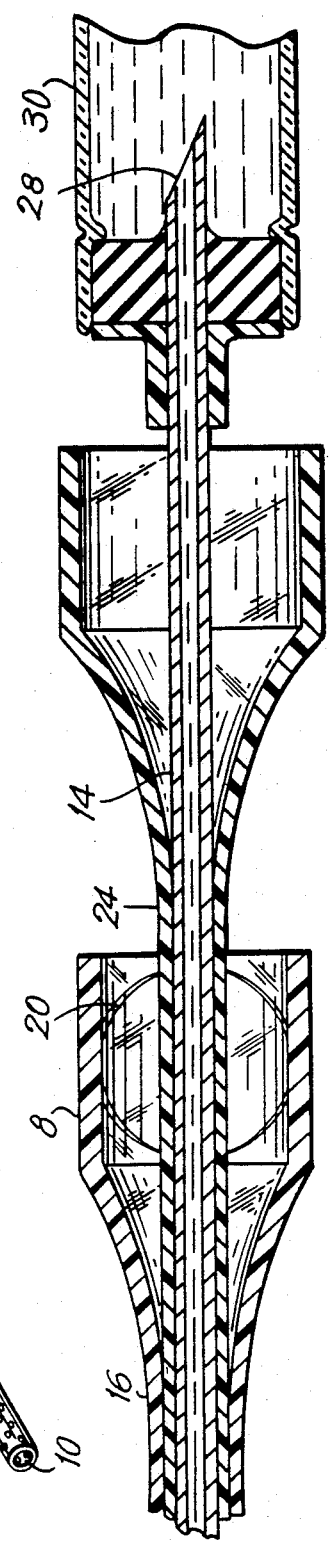

SAFETY NEEDLE SHEATH IN ANTI-REFLUX CATHETER HAVING NOVEL VALVE MEANS

CROSS-REFERENCE TO RELATED APPLICATIONS

This application is a continuation-in-part of application Ser. No. 050,589 filed May 15, 1987, now U.S. Pat. No. 4,784,644.

TECHNICAL FIELD

This invention relates to a valve, catheter and method for preventing both needle-stick injuries by possibly contaminated or infected needles and blood reflux onto the hands of healthcare workers. The invention can also be used to prevent blood from clotting within the tip of the catheter, thereby eliminating the problem of removing and replacing the

BACKGROUND

There is great concern among hospital personnel about the serious risks associated with the use of needles in the healthcare environment. Particularly, healthcare workers remain fearful of becoming infected with viruses such as the acquired immunodeficiency syndrome (AIDS) or hepatitis B as a consequence of having been exposed, directly or indirectly, to a patient's blood sample. These infectious agents are transmitted to the healthcare worker when, in the performance of his duty to collect blood from a patient, a needle stick is made or blood clotting develops within the tip of a previously inserted catheter. Whether it is when a hospital employee is punctured with the patient's needle or when the employee is exposed to the patient's blood while removing a clot from or replacing the catheter, the effect of this occupational hazard appears to be the same: potential medical and psychological consequences for both the healthcare worker and his family.

Healthcare workers have identified four specific circumstances under which the risk of contracting a virus from a patient's infected blood is extremely high: (1) while disassembling a device that has an exposed or contaminated needle; (2) while carrying exposed needles to a disposal box along with other items; (3) while storing a needle that is to be used two or more different times to collect blood from a patient; (4) while passing by another healthcare worker who is holding an exposed needle; or (5) leaving a contaminated needle in the patient's bed. In view of these circumstances, it appears that a solution to the problem is the development of a device that provides for the needle to remain unexposed when it is not being used to withdraw blood. In fact, the National Academy of Sciences Cmmmittee on Trauma Research has concluded that improvements in product design are among the most successful approaches to the prevention of injury in this area. Jagger, et al. "Rates of Needle-Stick Injury Caused By Various Devices In a University Hospital," The New England Journal of Medicine, Aug. 4, 1988, pp. 284–87.

Accordingly, the present invention is a new and effective means for preventing needle stick injuries, blood clotting, and catheter contamination. No other arrangement known heretofore is as practical or efficient in preventing the spread of viruses from patients to healthcare workers.

SUMMARY OF THE INVENTION

It is an object of the present invention to provide improved methods for preventing needle-stick injuries to health care workers during various intravenous or intraarterial procedures.

Another object of the invention relates to a method for preventing blood from clotting within the catheter.

Still another object of the invention relates to a method for preventing the reflux of fluids following the introduction of a catheter system into the vascular tree.

Thus, the present invention relates to a method for preventing needle exposure to healthcare workers during intravenous or intra-arterial procedures which comprises providing the catheter means having fluid flow control means, the fluid flow control means comprising a tubular structure and a valve means wherein the valve means is competent in response to blood reflux but opens in responses to a positive fluid pressure within the tubular structure, the catheter means also having needle-enveloping means including obturating means which is inserted into the tubular structure in order to render the valve means incompetent, needle means which is inserted into the obturating mans, and a receptacle means which is releasably secured to one end of the needle means. This method contemplates that the obturating means is made of a material which will not stick to the valve means and will facilitate insertion of the obturating means into the valve means as well as removal therefrom. This method further contemplates that the valve means comprises a tube having a flexible plastic disc therein. The needle means is double ended in order to permit one end thereof to pierce the vein or artery of a patient meanwhile allowing blood to collect in the receptacle means which is releasably secured to the other end of the needle means. The needle means may be retracted halfway within the obturating means before the needle means and obturating means are simultaneously withdrawn from within the tubular structure.

The invention also relates to a method for preventing blood from clotting within the catheter during intravenous or intra-arterial procedures which comprises providing the catheter means having fluid flow control means, the fluid flow control means comprising a tubular structure and a valve means wherein the valve means is competent in response to blood reflux but opens in response to a positive fluid pressure within the tubular structure, the catheter means also having needle-enveloping means including obturating means which is inserted into the tubular structure in order to render the valve means incompetent, needle means which is inserted into the obturating means, and a receptacle means which is releasably secured to one end of the needle means. The needle means is double-ended, one end of the needle means being inserted into a patient's blood vessel and the other end of the needle means being releasably secured to the receptacle means. The receptacle means collects blood which is directed under pressure through the needle means when the catheter means is inserted into a patient's blood vessel. The obturating means and needle means are simultaneously withdrawn from within the tubular structure after the needle means has first been retracted halfway within the obturating means so that no blood ever touches the hands of the inserting healthcare worker and any blood that refluxes up the needle means enters the receptable means. Blood collection is facilitated by a plurality of apertures located on the end of the tubular structure that is opposite to the end on which the receptacle means is releasably secured.

The methods of the invention advantageously utilize fluid flow control means comprising a tubular means with an input chamber and an output chamber and valve means located within the tubular means and having an open and closed position, the valve remaining competent in response to blood reflux but opens in response to a positive fluid pressure within the tubular means in order to render the valve means incompetent; and needle means having a first and second end, inserted into the obturating means to insert the fluid flow control means into an organ or the pleural cavity of a patient for removal of fluid therefrom, with the needle being retracted within the obturating means when the obturating means and needle means are simultaneously withdrawn from the tubular means so that only the tubular means remains in the organ or pleural cavity of the patient and said valve remains competent in response to fluid reflux. The valve means is integral with the tubular means. Further, the needle means is enveloped by the obturating means when the needle means is retracted within the overlying obturating means so that the needle means is unexposed.

BRIEF DESCRIPTION OF THE DRAWINGS

The nature, advantages, and various other additional features of the invention will appear more fully upon consideration of the illustrative embodiment now to be described in detail in connection with the accompanying drawing figures, wherein:

FIG. 2 is a perspective view of a catheter with valve means for draining fluids from the body; and FIG. 3 is a cross-sectional view of a catheter arrangement with fluid flow control means.

DETAILED DESCRIPTION OF THE PREFERRED EMBODIMENT

Figure 1:
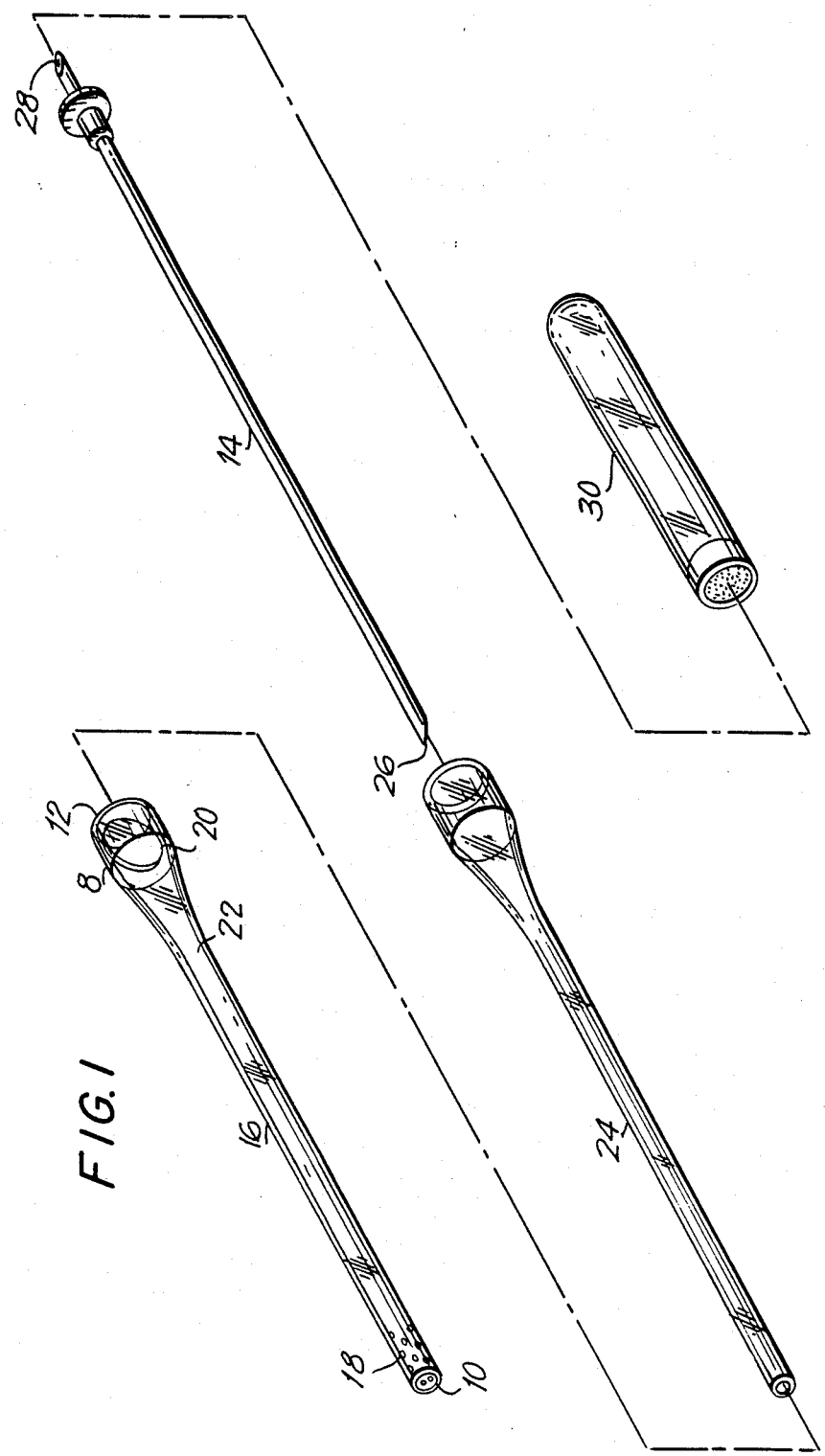
FIG. 1 is a perspective view of a catheter arrangement with fluid flow control means for removing fluids from the body.

In U.S. Pat. No. 4,684,364 there is disclosed a flow control device having a tubular structure with input means and output means each provided with an open bore, channel means connecting the input and output bores and operating between open and closed positions, and clip means for retaining a portion of the channel means in a prestressed condition to obturate the channels means so as to maintain it in a closed position. The channel means is forceable to an open position in response to a positive pressure in either one of the bores to facilitate flow through the channel means from the bore containing the positive pressure to the other bore. Also, the flow control device is capable of passing fluid in either direction depending upon which bore contains the positive pressure, with the clip means returning the channel means to the closed position when the positive fluid pressure is removed. This invention also includes an intravenous system comprising a source of intravenous fluid, first catheter means for insertion into the vascular system of a patient, a pump for performing a pumping operation and urging the fluid from the source to the first catheter means, second catheter means coupling the pump to the source, and the flow control device described above located in at least the first catheter means.

In U.S. Pat. No. 4,722,725, there is disclosed catheter means comprising an elongated body portion for insertion into a patient, at least one integral hub portion adjacent to the body portion, and at least one fluid flow control means located in either the body or hub portion or adjacent to the hub portion. The fluid flow control means may be integral with or releasably secured to its respective hub portion. Also, obturating means for rendering incompetent the fluid flow control means can be used.

The catheter means is intended for use in the methods disclosed in that patent. Such methods include preventing the introduction of ambient air into the vascular system of a patient when the catheter means is introduced into the patient's vascular system during intravenous or intra-arterial procedures, preventing the reflux of blood from the vascular system of the patient during such introvenous or intra-arterial procedures, and preventing the reflux of fluids into an organ or the pleural cavity of the patient when fluid directing means or catheter means are utilized for the removal of such fluids therefrom.

In U.S. Pat, No. 4,784,644, there is disclosed a novel valve comprising a disc member for use in a fluid flow control means. This fluid flow control means can be incorporated into a catheter and used for delivering or removing fluids from a patient To the extent that the disclosure of the specification or drawings of either of these patents is necessary for an understanding of the present invention, the disclosures of the patents are expressly incorporated herein by reference thereto.

FIGS. 1 and 2 generally illustrate a fluid flow control means in the form of a valve arrangement 8 provided with an inlet chamber 10 and an outlet chamber 12. The trocar portion of this arrangement 8 includes a strong sturdy needle 14. The catheter 16 includes a plurality of holes 18, valve 20, and compartment 22 for reception of an obturator 24 and the needle 14. In order to place the catheter 16 into the proper location in the patient's vascular system, the catheter 16, obturator 24 and needle 14 are inserted therein together. The needle 14 is provided with a sharp point 26 which assists in puncturing the skin and vein or artery of the patient, and a sharp point 28 upon which a vacutainer 30 is secured, in which the blood is collected. The obturator 24 is inserted into the catheter valve 20, thus it incompetent so as to allow blood to flow through the needle 14 and into the evacuated tube 30 or syringe (not shown) resulting in collection of the blood in the tube 30. One skilled in the art would realize that a syringe or other blood collection device could be used instead of the evacuated tube.

Following collection of blood in tube 30, the needle 14 is retracted into the obturator 24 and the needle 14 and obturator 24 are then simultaneously withdrawn from the catheter 16, allowing valve 20 to become competent, thus preventing blood reflux through the catheter proximal to the value 20, as well as needle-stick injuries because the needle 14 remains unexposed when withdrawn from the catheter 16 since it is enveloped by obturator 24, having been retracted therewithin.

FIG. 3 illustrates a cross-sectional view of the fluid flow control means in the form of a valve arrangement of FIGS. 1 and 2. The valve 20 is clearly shown as integral with the compartment 22 of the catheter 16.

While it is apparent that the invention herein disclosed is well calculated to fulfill the objects above stated, it will be appreciated that numerous embodiments and modifications may be devised by those skilled in the art, and it is intended that the appended claims cover all such modifications and embodiments as fall within the true spirit and scope of the present invention.

What is claimed is:

1. A method for preventing needle-stick injuries when catheter means is introduced into or withdrawn from the vascular system of a patient during intravenous or intraarterial procedures as well as during disposal, storage or transportation of the catheter means which comprises:

providing a catheter means having fluid flow control means and needle-enveloping means, said fluid flow control means comprising: a tubular structure including input means and output means, each provided with an open bore constituting a flow channel; valve means located between the bores of said input and output means of said tubular structure and having an open and closed position, said valve means providing for a connecting channel between said bores when said further means is in the open position, said further means normally being prestressed to said closed position and being forcible to said open position in response to a positive fluid pressure in the bore of either of said input or output means, said valve means being constructed and arranged so as to return to said closed position in response to a removal of said positive fluid pressure from said bore containing same; said needle-enveloping means including obturating means inserted into said tubular structure so as to render said valve means incompetent, needle means inserted into said obturating means, and receptacle means releasably securable to one end of said needle means;

introducing the catheter means having said inserted obturating means and needle means into an organ or pleural cavity of a patient for removal of fluids therefrom;

retracting the needle means within the overlying obturating means so that the obturating means envelops said needle means; and withdrawing simultaneously the retracted needle means and said obturating means with the needle means unexposed from within the tubular structure so that only said tubular structure remains in the organ or pleural cavity of said patient and said valve means remains competent in response to fluid reflux.

2. The method of claim 1 which further comprises making the obturating means of a material which will not stick to said valve means to facilitate insertion thereinto and removal therefrom.

3. The method of claim 1 wherein said valve means comprises a tube having a flexible plastic disc therein.

4. The method of claim 1 wherein the needle means is double-ended in order to permit piercing of the skin of a patient with the end of said needle means opposite said end having said releasably securable receptacle means.

5. The method of claim 1 wherein the end of the tubular structure opposite the releasably securable receptacle means includes a plurality of apertures to facilitate fluid collection or removal.

6. The method of claim 1 wherein said needle means is retracted half-way within said obturating means before the needle means and obturating means are simultaneously withdrawn from the tubular structure.

7. A method for preventing needle stick injuries when catheter means is introduced into or withdrawn from the vascular system of a patient during intravenous or intraarterial procedures as well as during disposal, storage or transportation of the catheter means which comprises: p1 providing a catheter means having fluid flow control means and needle-enveloping means, said fluid flow control means comprising: a tubular structure including input means and output means, each provided with an open bore constituting a flow channel; valve means located between the bores of said input and output means of said tubular structure and having an open and closed position, said valve means providing for a connecting channel between said bores when said valve means is in the open position, said valve means normally being prestressed to said closed position and being forcible to said open position in response to a positive fluid pressure in the bore of either of said input or output means, said valve means being constructed and arranged so as to return to said closed position in response to a removal of said positive fluid pressure from said bore containing same; said needle-enveloping means including obturating means inserted into said tubular structure so as to render said fluid flow control means incompetent, needle means inserted into said obturating means, and receptacle means releasably secured to one end of said needle means;

introducing the catheter means with said inserted obturating means and needle means into a blood vessel of a patient for removal of blood therefrom;

retracting the needle means within the overlying obturating means so that the obturating means envelops said needle means; and withdrawing simultaneously the retracted needle means and said obturating means with needle means unexposed from within the tubular structure so that only said tubular structure remains in the blood vessel of said patient and said valve means remains competent in response to blood reflux.

8. The method of claim 7 wherein the needle means is double-ended in order to permit insertion of a first end of the needle into the blood vessel of a patient with the second end capable of releasably securing the receptacle means thereto.

9. The method of claim 7 wherein the end of the tubular structure opposite the releasably secured receptacle means includes a plurality of apertures to facilitate blood collection or removal.

10. The method of claim 7 wherein the obturating means and needle means are simultaneously withdrawn from within the tubular structure after said needle means has first been retracted half-way within the obturating means so as to avoid blood contact with the user of the catheter means.

11. The method of claim 7 wherein an intravenous system is attached to the tubular means for introduction of fluids through said tubular structure after withdrawal of the obturating means and needle means therefrom.

12. The method of claim 7 wherein the receptacle means includes a vacuum therein to collect blood through the needle means when the catheter means is inserted into a blood vessel of the patient.

13. Fluid flow control means comprising:

tubular means having input means and output means, each provided with an open bore constituting a flow channel, valve means located between the bores of said input and output means of said tubular structure and having an open and closed position, said valve means providing for a connecting channel between said bores when said valve means is in the open position, said valve means normally being prestressed to said closed position and being forcible to said open position in response to a positive fluid pressure in the bore of either of said input or output means, said valve means being constructed and arranged so as to return to said closed position in response to a removal of said positive fluid pressure from said bore containing same;

obturating means, inserted into said tubular means so as to render incompetent said valve means; and needle means having a first and second end, inserted into said obturating means to insert the fluid flow control means into an organ or the pleural cavity of a patient for removal of fluid therefrom, with the needle being retracted within the obturating means when the obturating means and needle means are simultaneously withdrawn from the tubular means, so that only the tubular means remains in the organ or pleural cavity of said patient and said valve means remains competent in response to fluid reflux.

14. The fluid flow control means of claim 13 wherein said needle means comprises a first end and a second end, the first end being inserted into the organ or pleural cavity of the patient, with the second end capable of releasably securing said receptacle means thereto.

15. The fluid flow control means of claim 14 wherein the tubular means comprises a first end and a second end, the first end of said tubular means being inserted into the organ or pleural cavity of the patient, wherein said first end comprises a plurality of apertures to facilitate fluid collection or removal.

16. The fluid flow control means of claim 13 wherein said valve means is integral with said tubular means.

17. The fluid flow control means of claim 13 wherein said needle means is enveloped by said obturating means when said needle means is retracted within the overlying obturating means so that the needle means is unexposed.

18. The fluid flow control means of claim 13 wherein said valve means includes a disc member position within a flexible tube.

19. The fluid flow control means of claim 13 wherein said obturating means is a trocar which houses said needle means therein.

20. The fluid flow control means of claim 13 wherein said trocar includes means for preventing insertion of said needle means beyond a predetermined distance therein.

* * * * *